United States Patent
Kuzuhara et al.

(10) Patent No.: US 7,553,994 B2
(45) Date of Patent: Jun. 30, 2009

(54) METHOD FOR PRODUCING DITRIMETHYLOLPROPANE

(75) Inventors: Ikutaro Kuzuhara, Okayama (JP); Atsushi Iwamoto, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/641,104

(22) Filed: Dec. 19, 2006

(65) Prior Publication Data
US 2007/0191646 A1 Aug. 16, 2007

Related U.S. Application Data

(63) Continuation of application No. 10/864,635, filed on Jun. 10, 2004, now abandoned.

(30) Foreign Application Priority Data
Jun. 13, 2003 (JP) .............................. 2003-169573

(51) Int. Cl.
C07C 41/58 (2006.01)

(52) U.S. Cl. ...................................... 568/680; 568/699

(58) Field of Classification Search .................. None
See application file for complete search history.

(56) References Cited

U.S. PATENT DOCUMENTS

| 3,740,322 A | * | 6/1973 | Wada et al. ................... 203/48 |
| 3,829,507 A | | 8/1974 | Zey |
| 2002/0033325 A1 | | 3/2002 | Ninomiya et al. |

FOREIGN PATENT DOCUMENTS

| EP | 1178030 | 2/2002 |
| GB | 1292405 | 10/1972 |
| JP | 2002-047231 | 2/2002 |
| JP | 2002-047232 | 2/2002 |

OTHER PUBLICATIONS

Communication and European Search Report dated Dec. 11, 2004, for No. EP 04 01 3343.

* cited by examiner

*Primary Examiner*—Rosalynd Keys
(74) *Attorney, Agent, or Firm*—Antonelli, Terry, Stout & Kraus, LLP.

(57) ABSTRACT

In the method of producing ditrimethylolpropane of the present invention, the distillation still residue obtained in the production of trimethylolpropane is subjected to crystallizing treatment while strictly regulating the amount of organic solvent to be used, the crystallization temperature and the crystallization time within the specific ranges. With the method of the present invention, a highly pure di-TMP is obtained only by a single operation of the crystallization.

9 Claims, No Drawings

METHOD FOR PRODUCING DITRIMETHYLOLPROPANE

This application is a Continuation application of application Ser. No. 10/864,635, filed Jun. 10, 2004 now abandoned, the contents of which are incorporated herein by reference in their entirety.

BACKGROUND OF THE INVENTION

1. Field of the Invention

The present invention relates to a novel method for producing ditrimethylolpropane (hereinafter referred to as "di-TMP").

2. Description of the Prior Art

Highly pure di-TMP has been used as the raw materials for the production of polyacrylate, polyether polyol, polyurethane, alkyd resin, synthetic lubricating oil, etc. di-TMP is by-produced and recovered in the industrial production of trimethylolpropane (hereinafter referred to as "TMP") by aldol condensation and crossed Cannizzaro reaction of n-butyl aldehyde (hereinafter referred to as "NBD") and formaldehyde (for example, U.S. Pat. No. 3,097,245). In the proposed method, a TMP extract (crude TMP) containing substantially no sodium formate is obtained by extracting the reaction product solution of the reaction of NBD and formaldehyde with a solvent, after condensing or without condensing the reaction product solution. The purification of the crude TMP by high vacuum distillation leaves a still residue containing 1 to 20% of TMP and 20 to 50% di-TMP. To recover di-TMP from the still residue, there have been proposed crystallization from ethyl acetate (for example, Japanese Patent Application Laid-Open No. 47-30611), crystallization from water in the presence of sodium formate (for example, Japanese Patent Application Laid-Open No. 49-133311), crystallization from 1,4-dioxane (for example, Japanese Patent Application Laid-Open No. 2002-47231), etc.

However, only by the crystallization from the organic solvent such as ethyl acetate, a highly pure di-TMP is not obtained from the distillation still residue in the production of TMP. When the distillation still residue is colored, the contamination of di-TMP with colored substances is not prevented in the crystallization from water. Therefore, to obtain a highly pure di-TMP, the crystallizing operation should be repeated in these methods.

It is reported that the crystallization from 1,4-dioxane enables the recovery of a highly pure di-TMP only in one crystallizing operation. However, 1,4-dioxane is toxic and easily converted into explosive peroxide by the reaction with oxygen in air. Therefore, it is desirable to avoid the use of 1,4-dioxane as much as possible in the industrial process, because there is a danger of explosion during the recovery of 1,4-dioxane for reuse by distilling the filtrate after the crystallization.

SUMMARY OF THE INVENTION

An object of the present invention is to provide an efficient and safe method for separating and recovering a highly pure di-TMP free from the contamination with colored substances from the distillation still residue in the production of TMP.

A highly pure di-TMP is not obtained only by a single operation of crystallization from a general-purpose organic solvent including ketones such as acetone and methyl ethyl ketone, and esters such as ethyl acetate and butyl acetate. This is because of the difficulty to separate a linear formal formed from two moles of TMP and formaldehyde (hereinafter referred to as "bis-TMP") each present in the distillation still residue of the crude TMP. As a result of extensive research in view of solving the above problem, the inventors have found that, by strictly regulating the amount of the solvent to be added to the distillation still reside, the crystallization temperature and the crystallization time within specific ranges, bis-TMP is separated with great efficiency and a colorless, highly pure di-TMP is easily and safely obtained only by a single operation of crystallization. The present invention has been accomplished on the basis of this finding.

Thus, the present invention provides a method for producing ditrimethylolpropane represented by the following formula 1:

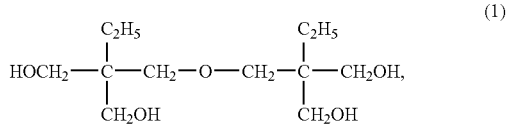

the method comprising:
a step of reacting n-butyl aldehyde and formaldehyde in the presence of a basic catalyst to obtain a reaction product solution;
a step of extracting the reaction production solution with an organic extractant to obtain an extract;
a step of distilling the extract to separate trimethylolpropane as a distillate and obtain a distillation still residue; and
a step of adding an organic solvent to the distillation still residue in an amount of 0.6 to 10 times a weight of the distillation still residue, and treating the solvent-added distillation still residue at a crystallization temperature Y ° C. satisfying the following formula 3:

$$(30 \times \ln(X) - 92) \leq Y \leq 55 \quad (3)$$

wherein X is a percent by weight concentration of ditrimethylolpropane in the distillation still residue before adding the organic solvent, for 0.1 to 20 h, thereby crystallizing ditrimethylolpropane.

DETAILED DESCRIPTION OF THE INVENTION

The aimed compound of the present invention, ditrimethylolpropane (di-TMP) is represented by the following formula 1:

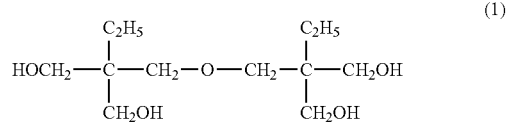

and bistrimethylolpropane (bis-TMP) is represented by the following formula 2:

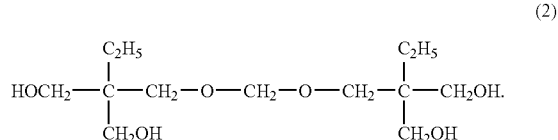

The distillation still residue to be treated in the present invention is obtained in the following manner.

By reacting NBD and formaldehyde in the presence of a basic catalyst in a manner described, for example, in Japanese Patent Application Laid-Open No. 11-49708, a reaction production solution is obtained, which is then extracted with an organic extractant after condensing or without condensing the reaction product solution to obtain a TMP extract containing substantially no sodium formate. Examples of the extractants include aliphatic esters such as ethyl acetate and butyl acetate; aliphatic ketones such as methyl ethyl ketone, methyl isobutyl ketone and diisopropyl ketone; alcohols such as isobutyl alcohol, amyl alcohol, hexyl alcohol and cyclohexyl alcohol; and aldehydes such as isobutyl aldehyde and n-butyl aldehyde. These extractants may be used alone or in combination of two or more. The amount of the extractant to be used and the extraction conditions are not specifically limited, and the extracting operation is generally performed at 5 to 55° C. using the extractant in an amount of 0.5 to 5 times the weight of the reaction product solution.

The TMP extract is distilled to remove the organic extract to obtain a crude TMP, which is further distilled under high vacuum (0.1 to 5 KPa), thereby separated into TMP and the distillation still residue. The concentration of di-TMP in the distillation still residue is preferably about 20 to about 90% by weight. In the present invention, the distillation still residue thus obtained is directly added with an organic solvent and subjected to crystallization under specific conditions to recover di-TMP.

Examples of the organic solvents for crystallization include aliphatic ketones, aliphatic esters and tetrahydrofuran, with the aliphatic ketones and aliphatic esters being preferred, and ethyl acetate, methyl ethyl ketone and acetone being more preferred. These organic solvents available as industrial products can be used as-received without purification.

The amount of the organic solvent to be used is 0.6 to 10 times, preferably 0.8 to 5 times, more preferably 1 to 3 times the weight of the distillation still residue. If less than 0.6 times, TMP and bis-TMP are crystallized together with di-TMP and the contamination with colored substances is not avoided to reduce the purity of di-TMP crystals. If exceeding 10 times, the yield of di-TMP crystals is reduced or di-TMP is not crystallized. In addition, the load for recovering the organic solvent becomes excessively large to make the process industrially disadvantageous.

The crystallization temperature is $Y$ ° C. satisfying the following formula 3:

$$(30 \times \ln(X) - 92) \leq Y \leq 55 \tag{3}$$

wherein X is a percent by weight concentration of ditrimethylolpropane in the distillation still residue before adding the organic solvent. If higher than the above range, the yield of di-TMP crystals is reduced or di-TMP is not crystallized. If lower than the above range, bis-TMP is crystallized in a large amount in addition to di-TMP to extremely reduce the purity of di-TMP crystals.

The crystallization time is 0.1 to 20 h, preferably 0.5 to 10 h, and more preferably 1 to 4.5 h. If shorter than 0.1 h, the yield of di-TMP crystals is reduced or di-TMP is not crystallized. If longer than 20 h, bis-TMP is crystallized together with di-TMP to reduce the purity of di-TMP crystals. In addition, the apparatus efficiency is lowered to make the process industrially disadvantageous.

After added with the organic solvent, the distillation still residue is stirred until a transparent solution is obtained optionally under heating, for example, under heating to 56 to 60° C. Thereafter the distillation still residue is cooled to the crystallization temperature while continuing the stirring to allow the crystallization to take place. After the crystallization time specified above is passed, di-TMP crystals are separated from the resultant slurry by filtration, centrifugation, etc., washed with the organic solvent and dried to obtain highly pure, preferably 94 to 100% purity (weight basis) of di-TMP crystals.

The organic solvent recovered by distilling the filtrate and washings obtained in the crystallization step may be reused as the solvent for recrystallization together with the organic solvent recovered during the drying operation of di-TMP crystals.

In the present invention, by subjecting the distillation still residue obtained after the distillation of TMP to the crystallization treatment under the amount of the organic solvent, crystallization temperature and crystallization time which are regulated within the specific ranges, di-TMP which is free from bis-TMP and colored substances even when the Gardner color scale of the distillation still residue is 10 or more is obtained from the distillation still residue with great efficiency only by a single operation of the crystallization.

The present invention will be explained in more detail by reference to the following examples which should not be construed to limit the scope of the present invention.

In the following examples and comparative examples, the degree of coloring was measured according to JIS K 0071-2 (Gardner color scale) and JIS K 1510 (phthalic acid resin color). The percentage and ppm are based on weight.

PRODUCTION EXAMPLE

In accordance with the procedure of Example 1 described in Japanese Patent Application Laid-Open No. 11-49708, NBD and formaldehyde were reacted to produce TMP. After completing the reaction, TMP was extracted from the reaction production solution with NBD as the extractant. After recovering or removing low-boiling starting materials and by-products, the extract (crude TMP) was distilled by a film evaporator to obtain a distillation still residue. The composition of the distillation still residue is shown below.

| | |
|---|---|
| TMP | 7.7% |
| di-TMP | 44.7% |
| bis-TMP | 27.4% |
| Organic by-products | 19.9% |
| Salts | 3000 ppm |
| Gardner color scale | 10 |

EXAMPLE 1

In a 3000-mL round bottom flask equipped with a mechanical stirring device, 1300 g of the distillation still residue obtained above and 1300 g of acetone were stirred under heating until the mixture changed to a transparent solution. Then, the solution was cooled to 30° C. under stirring and subjected to the crystallizing treatment for 2 h while keeping the temperature at 30° C. Crystals separated from the resultant slurry by centrifugation were washed with 250 g of acetone and dried to obtain 256 g of crystals. The obtained crystals showed a di-TMP purity of 96%, a melting point of 109° C. and a phthalic acid resin color of 1.

EXAMPLE 2

In a 1000-mL round bottom flask equipped with a mechanical stirring device, 250 g of the distillation still residue obtained above and 500 g of ethyl acetate were stirred under heating until the mixture changed to a transparent solution. Then, the solution was cooled to 40° C. under stirring and subjected to the crystallizing treatment for 1.5 h while keeping the temperature at 40° C. Crystals separated from the resultant slurry by suction filtration were washed with 40 g of ethyl acetate and dried to obtain 40 g of crystals. The obtained crystals showed a di-TMP purity of 96%, a melting point of 109° C. and a phthalic acid resin color of 1.

Comparative Example 1

In the same manner as in Example 1 except for changing the amount of acetone used to 650 g, 314 g of crystals were obtained. The obtained crystals showed a di-TMP purity of 86%, a melting point of 96° C. and a phthalic acid resin color of 3.

Comparative Example 2

In the same manner as in Example 1 except for changing the crystallization temperature to −5° C., 689 g of crystals were obtained. The obtained crystals showed a di-TMP purity of 56%, a melting point of 83° C. and a phthalic acid resin color of 5.

Comparative Example 3

In the same manner as in Example 1 except for changing the crystallization time to 25 h, 291 g of crystals were obtained. The obtained crystals showed a di-TMP purity of 90%, a melting point of 104° C. and a phthalic acid resin color of 2.

As described above, in the method of the present invention, the distillation still residue in the production of trimethylolpropane is subjected to crystallizing treatment while strictly regulating the amount of organic solvent to be used, the crystallization temperature and the crystallization time within the specific ranges. With such a method, a highly pure di-TMP is obtained only by a single operation of the crystallization. Thus, the present invention is of great industrial advantage.

What is claimed is:

1. A method for producing ditrimethylolpropane represented by the following formula 1:

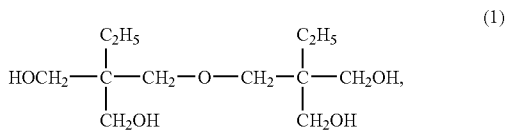

(1)

which has a melting point of 109° C., a phthalic acid resin color of 1.0, and a purity of 96 to 100%,
the method comprising:
a step of reacting n-butyl aldehyde and formaldehyde in the presence of a basic catalyst to obtain a reaction product solution;
a step of extracting the reaction product solution with an organic extractant to obtain an extract;
a step of distilling the extract to separate trimethylolpropane as a distillate and obtain a distillation still residue; and
directly after said step of distilling, a step of adding an organic solvent to the distillation still residue in an amount of 0.6 to 10 times a weight of the distillation still residue, the organic solvent being at least one compound selected from the group consisting of acetone and methyl ethyl ketone, and
a step of crystallizing said ditrimethylolpropane from the distillation still residue, in a single crystallization operation, which is only a single crystallization operation, at a crystallization temperature Y ° C. satisfying the following formula 3:

$$30 \leq Y \leq 40 \quad (3)$$

for 1.5 to 2h, thereby crystallizing said ditrimethylolpropane having said melting point, said phthalic acid resin color and said purity, by only said single crystallization operation.

2. The method according to claim 1, wherein concentration of ditrimethylolpropane in said distillation still residue is 20 to 90% by weight.

3. The method according to claim 1, wherein the amount of organic solvent added to the distillation still residue is 0.8 to 5 times the weight of the distillation still residue.

4. The method according to claim 3, wherein the amount of the organic solvent added to the distillation still residue is 1 to 3 times the weight of the distillation still residue.

5. The method according to claim 1, wherein the organic extractant is at least one compound selected from the group consisting of methyl ethyl ketone and ethyl acetate.

6. The method according to claim 1 wherein directly after the step of distilling the organic solvent is added to the distillation still residue to form a mixture, and the mixture is treated by said single crystallization operation.

7. The method according to claim 6, wherein between adding the organic solvent and treating the mixture by said single crystallization operation, the distillation still residue and organic solvent are heated and stirred.

8. A method for producing ditrimethylolpropane represented by the following formula 1:

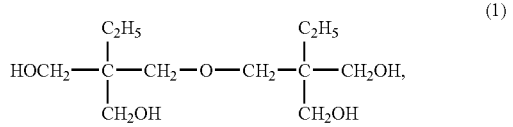

(1)

which has a melting point of 109° C., a phthalic acid resin color of 1.0, and a purity of 96 to 100%,
the method comprising:
a step of reacting n-butyl aldehyde and formaldehyde in the presence of a basic catalyst to obtain a reaction product solution;
a step of extracting the reaction product solution with an organic extractant to obtain an extract;
a step of distilling the extract to separate trimethylolpropane as a distillate and obtain a distillation still residue; and
directly after said step of distilling, a step of adding an organic solvent to the distillation still residue in an amount of 0.6 to 10 times a weight of the distillation still residue, the organic solvent being at least one compound selected from the group consisting of acetone and methyl ethyl ketone, and
a step of crystallizing said ditrimethylolpropane from the distillation still residue, in a single crystallization operation, which is only a single crystallization operation, at a crystallization temperature Y ° C. satisfying the following formula 3:

$$(30 \times \ln(X) - 84) \leq Y \leq 55 \quad (3)$$

wherein X in a percent by weight concentration of ditrimethylolpropane in the distillation still residue before adding the organic solvent,
for 1.5 to 2h, thereby crystallizing said ditrimethylolpropane having said melting point, said phthalic acid resin color and said purity, by only said single crystallization operation.

9. A method for producing ditrimethylolpropane represented by the following formula 1:

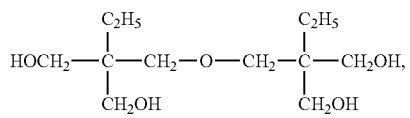

(1)

which has a melting point of 109° C., a phthalic acid resin color of 1.0, and a purity of 96 to 100%,
the method comprising:
a step of reacting n-butyl aldehyde and formaldehyde in the presence of a basic catalyst to obtain a reaction product solution;
a step of extracting the reaction product solution with an organic extractant to obtain an extract;
a step of distilling the extract to separate trimethylolpropane as a distillate and obtain a distillation still residue; and
directly after said step of distilling, a step of adding an organic solvent to the distillation still residue in an amount of 0.6 to 10 times a weight of the distillation still residue, the organic solvent being at least one compound selected from the group consisting of acetone and methyl ethyl ketone, and
a step of crystallizing said ditrimethylolpropane from the distillation still residue, in a single crystallization operation, which is only a single crystallization operation, at a crystallization temperature $Y$ ° C. satisfying the following formula 3:

$$(30 \times \ln(X) - 74) \leq Y \leq 55 \tag{3}$$

wherein X is a percent by weight concentration of ditrimethylolpropane in the distillation still residue before adding the organic solvent, for 1.5 to 2h, thereby crystallizing said ditrimethylolpropane having said melting point, said phthalic acid resin color and said purity, by only said single crystallization operation.

* * * * *